United States Patent [19]

Margulis et al.

[11] Patent Number: 5,392,239
[45] Date of Patent: Feb. 21, 1995

[54] BURST-MODE DRAM

[75] Inventors: Neal D. Margulis, Santa Clara; Takatoshi Ishii, Sunnyvale, both of Calif.

[73] Assignee: S3, Incorporated, Santa Clara, Calif.

[21] Appl. No.: 59,029

[22] Filed: May 6, 1993

[51] Int. Cl.⁶ .............................................. G11C 7/00
[52] U.S. Cl. ........................ 365/189.01; 365/189.05; 365/230.01; 365/230.03; 365/230.08; 365/233
[58] Field of Search ...................... 365/189.01, 230.01, 365/189.05, 230.03, 233, 235, 230.08; 364/200; 395/400, 425

[56] References Cited

U.S. PATENT DOCUMENTS

| | | | |
|---|---|---|---|
| 4,567,579 | 1/1986 | Patel et al. | 365/189 |
| 4,685,089 | 8/1987 | Patel et al. | 365/233 |
| 4,788,667 | 11/1988 | Nakano et al. | 365/193 |
| 4,789,966 | 12/1988 | Ozaki | 365/189 |
| 4,870,622 | 9/1989 | Aria et al. | 365/230.02 |
| 4,951,246 | 8/1990 | Fromm et al. | 364/900 |
| 5,058,005 | 10/1991 | Culley | 364/200 |
| 5,268,865 | 12/1993 | Takasugi | 365/236 |

OTHER PUBLICATIONS

Jones et al., "Fast Dynamic RAMs," *IEEE Spectrum*, Oct. 1992, pp. 44–45.
"256K×16 DRAM Fast Page Mode," Micron Technology, Inc., 1992, pp. 2-169–2-190.

*Primary Examiner*—Viet Q. Nguyen
*Assistant Examiner*—Huan Hoang
*Attorney, Agent, or Firm*—Dennis S. Fernandez; Phong K. Truong

[57] ABSTRACT

A dynamic random access memory (DRAM) circuit operates in burst mode when a row address strobe ($\overline{RAS}$) signal is applied while an output enable/burst enable signal is also applied thereto. During burst mode, a column address strobe ($\overline{CAS}$) signal is toggled to access digital data from sequential column addresses within a given row.

10 Claims, 6 Drawing Sheets

5,392,239

BURST-MODE DRAM

BACKGROUND OF THE INVENTION

1. Field of the Invention

This invention relates to electronic storage devices, particularly to dynamic random access memory (DRAM) circuits.

2. Description of the Background Art

DRAMs are used widely in various electronic systems for storing large amounts of digital information. However, as such electronic systems operate at faster processing speeds, the access time for reading or writing data to or from DRAMs becomes a significant factor in the design of high-performance electronic systems.

Hence, various techniques are used for improving DRAM access times. One approach known as "nibble mode" significantly reduces access time delays by configuring a DRAM to access a series of four sequential bits in rapid succession after a first bit is accessed. Similarly, in an approach known as "burst mode," a full page or row of bits are accessed after the first bit is accessed. These approaches improve DRAM access time by essentially eliminating address re-loading delays associated with accessing each subsequent bit. Typically, neither normal nor burst/nibble mode is selectable by certain control signals.

Current nibble and burst mode techniques, however, generally operate under special modes and are thus limited to operating with asynchronous clock and address signals to access data bits. It would be desirable, therefore, to provide an improved approach in reducing DRAM access time without such asynchronous addressing overhead and particularly to provide an improved scheme for selecting operating modes.

SUMMARY OF THE INVENTION

The invention resides in operating an improved storage device in burst mode by applying a row address strobe ($\overline{RAS}$) signal under selected times or conditions, such as while a burst enable signal is also applied thereto. Preferably, the storage device is a dynamic random access memory (DRAM) circuit wherein the burst enable signal comprises an output enable signal of the DRAM circuit.

Additionally during burst mode, a column address strobe ($\overline{CAS}$) signal may be toggled to access digital data from sequential column addresses within a given row address of the DRAM circuit.

DESCRIPTION OF THE PREFERRED EMBODIMENT

Figure 1:
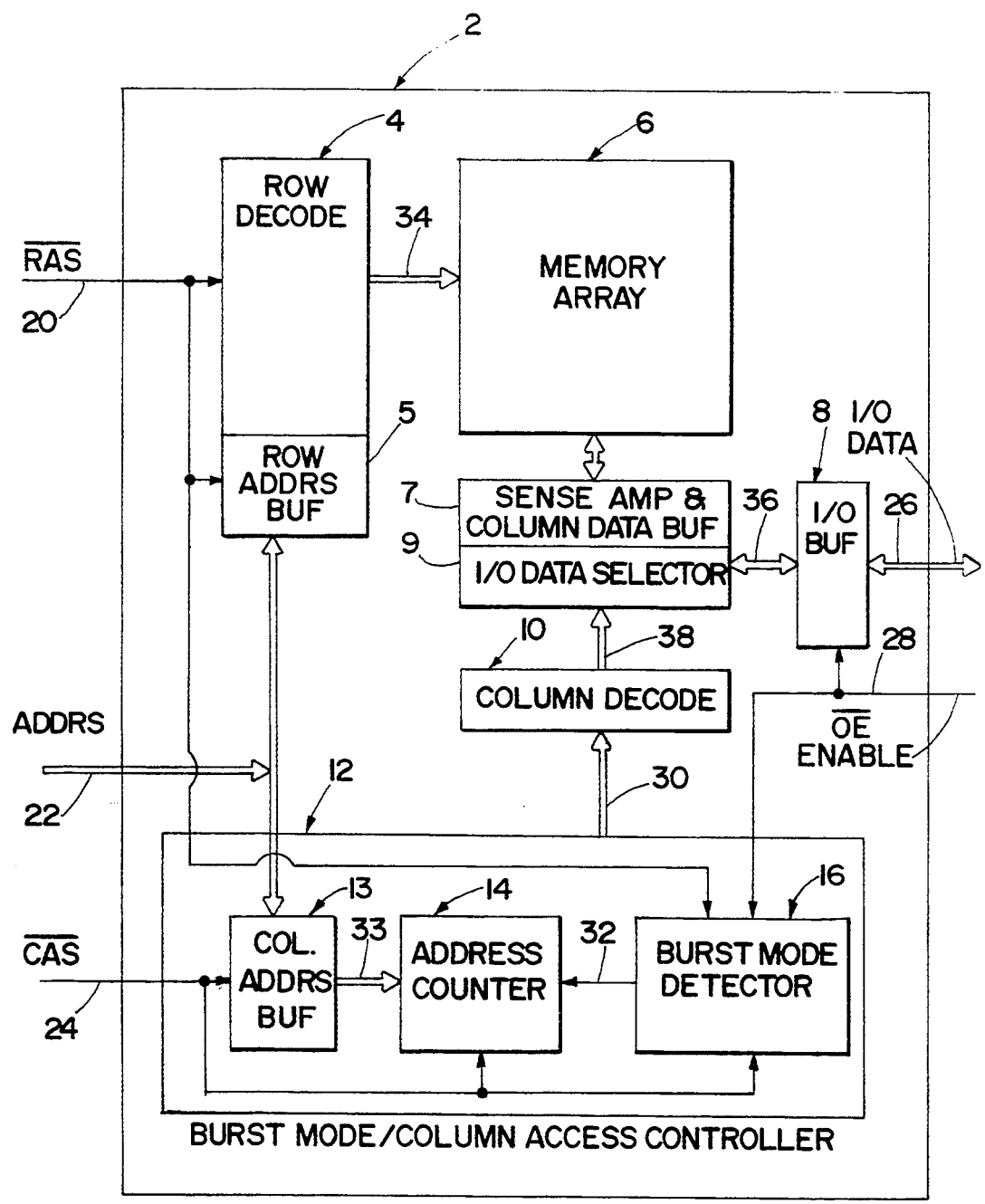
FIG. 1 is a block diagram of memory circuit 2 including burst mode controller 12 and memory array 6 coupled to row decode and column decode 10 circuits.

FIG. 1 is a block diagram of storage device or memory circuit 2, which preferably is an asynchronously-accessible dynamic random access memory (DRAM) integrated circuit having conventional memory array 6 including digital storage locations arranged in rows and columns and accessible 34, 38, 36, 30 through row decoder circuit 4, column decoder circuit 10, and input-/output (I/O) data buffer 8.

Preferably, conventional sense amplifier and column data buffer circuit 7 and input/output data selector 9 coupled thereto are coupled 36, 38 respectively to I/O buffer 8 and column decode circuit 10. Also, preferably, address signals 22 is received by memory circuit 2 at row address buffer circuit 5 in row decode circuit 4 and at column address buffer circuit 13 in burst mode/-column access controller circuit 12.

In accordance with the present invention, burst mode controller 12, which includes burst mode or signal detector 16 and column address buffer 13, both of which are coupled 32, 33 to address counter 14, enables operating memory circuit 2 in burst mode cycle 72, 73, 110. It is contemplated that address counter 14 may be implemented as well by equivalent address incrementing (or decrementing) circuits, such as a shifter, rotator, or ring counter. Additionally, to achieve access time improvements, it is contemplated that burst mode controller 12, and particularly address counter 14, are integrated in a common semiconductor substrate or chip as memory array 6 and other circuits 4, 5, 7, 8, 9, 10 in memory circuit 2.

As shown, memory circuit 2 receives row address strobe ($\overline{RAS}$) signal 20, 80, which is received by row decoder circuit 4 and burst mode detector 16; column address strobe ($\overline{CAS}$) signal 24, 81 which is received by column address buffer circuit 13, address counter 14 and burst mode detector 16; burst enable/output enable ($\overline{BE/OE}$) signal 28, 83 which is received by I/O buffer 8 and burst mode detector 16; and input/output (I/O) data signal 26, 85 which is receivable bi-directionally by I/O buffer 8.

Furthermore, in an alternate embodiment, it is contemplated that memory circuit 2 is provided as a specialized dual-port memory circuit, such as a video random access memory (VRAM). In this configuration, burst mode controller 12 may be integrated in or coupled to certain signal lines or ports of such VRAM. Preferably, in lieu of receiving $\overline{BE/OE}$ signal 28, 83, burst mode controller 12 may receive a single or combination of signal(s) to indicate a similar burst mode function.

Figure 2:
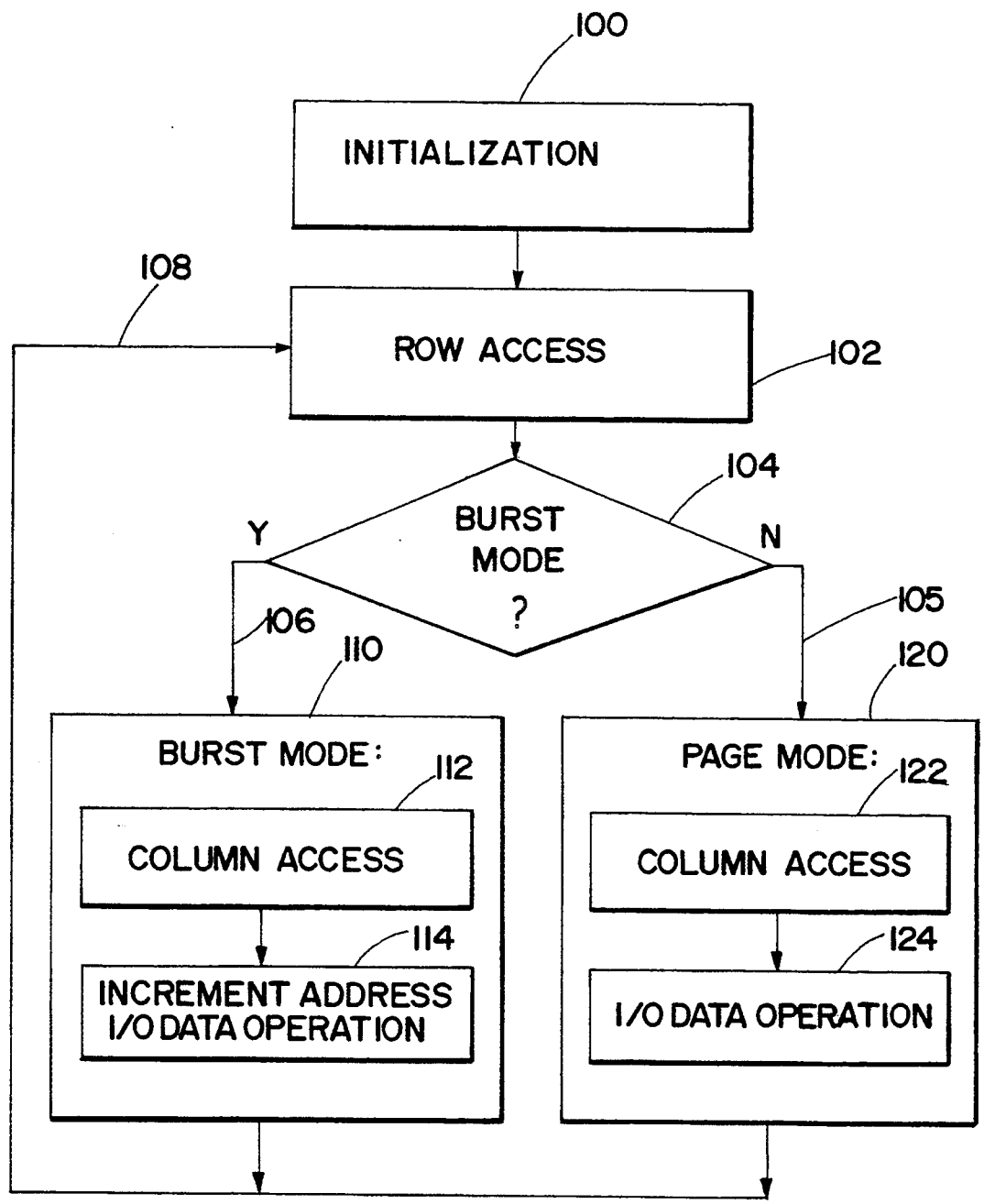
FIG. 2 is a flow chart of a process for operating memory circuit 2 in burst mode 72, 73, 110 or page mode 70, 71, 120.

FIG. 2 is a generalized flow chart of a process for operating memory circuit 2 in burst mode 72, 73, 110 or page mode 70, 71, 120. At initialization 100, memory circuit 2 is provided for accessing (i.e., reading or writing) addressable locations which may store digital data. Preferably after or during initialization step 100, an indication is provided to memory circuit 2 as to whether a memory access cycle is being invoked, either in burst mode 72, 73, 110 or in page mode 70, 71, 120. This indication is provided by asserting or applying $\overline{BE/OE}$ signal 28, 83 either as a logic level low (i.e., burst mode) or a logic level high (i.e., page mode).

After initialization 100, row access 102 occurs when first or row address signal 22, 75, 82, which indicates a particular row address therein, is applied to memory circuit 2, preferably while $\overline{BE/OE}$ signal 28, 83 is applied 51, 57. $\overline{RAS}$ signal 20, 80 is applied 70 to apply row address signal 22, 75, 82. At that time, burst mode controller 12 in memory circuit 2 then determines 104 what type of memory access cycle is being invoked, preferably by monitoring or sampling the signal state or level of $\overline{BE/OE}$ signal 28, 83 when $\overline{RAS}$ signal 20, 80 is applied 70.

If $\overline{BE/OE}$ signal 28, 83 is high (i.e., digital "1") when $\overline{RAS}$ signal 20, 80 is asserted 70, preferably low, then page mode 70, 71, 120 is invoked or defined 120. During page mode 70, 71, 120, digital storage locations in memory circuit 2 may be accessed initially by accessing a particular row address 22, 75, 82, and then accessing certain column addresses 22, 76, 82 to access digital storage locations having addresses on the same row, but on different columns.

Alternately, if $\overline{BE/OE}$ signal 28, 83 is low (i.e., digital "0") when $\overline{RAS}$ signal 20, 80 is asserted 70, preferably low, then burst mode 72, 73, 110 is invoked or defined 106. During burst mode 72, 73, 110, digital storage locations in memory circuit 2 may be accessed by initially accessing a particular row address 22, 75, 82, and then accessing a single column address 22, 76, 82 to access digital storage locations having addresses on the same row but on different, preferably subsequent or adjacent, columns.

Preferably, during burst mode 72, 73, 110, $\overline{BE/OE}$ signal 28, 83 is applied relative to $\overline{RAS}$ signal 20, 80 according to specified set-up and hold times. Additionally, either burst mode 72, 73, 110 or page mode 70, 71, 120 may be terminated when RAS signal 20, 80 is subsequently disabled or de-asserted, preferably in a high state. After such termination, row access step 102 may be repeated 108.

During either burst mode 72, 73, 110 or page mode 70, 71, 120, column access 112, 122 occurs when second or column address signal 22, 76, 82, which indicates a particular column address therein, is applied to memory circuit 2. $\overline{CAS}$ signal 24, 81 is applied 171 to column address buffer 13 to receive column address signal 22, 76, 82. After column access 112, 122 occurs in modes 110, 120, input/output (I/O) data operation 114, 124 may occur, wherein enable signal 28 is applied either in conventional input or output enable mode. In step 114, both address incrementing and I/O data operation occur.

Thus, particular digital storage locations, as specified preferably by rows and columns arranged in a matrix, in memory circuit 2 are accessible for reading or writing data by accessing particular rows 102 and accessing particular columns 112, 122, in accordance with row address signals 22, 75, 82 and column address signals 22, 76, 82.

When operating in accordance with the present invention, burst mode controller 12 causes burst mode detector 16 to detect the levels or states of $\overline{BE/OE}$ signal 28, 83 and $\overline{RAS}$ signal 20, 80 as applied to memory circuit 2 to define burst mode 72, 73, 110. In addition, address counter 14 in burst mode controller 12 increments (or decrements) 114 an accessed column address received 33 from column address buffer 13 and stored therein when column access 112 occurs, i.e., when $\overline{CAS}$ signal 24, 81 is applied or toggled 171, 172, 173, 174, during burst mode 72, 73, 100. Timing for address incrementing may be changed according to each particular memory circuit 2 configuration.

Thus, when $\overline{CAS}$ signal 24, 81 is toggled, preferably as detected by burst mode detector 16 during $\overline{CAS}$ signal 24, 81 falling edges, during burst mode 72, 73, 110, digital data stored in memory circuit 2 are accessible according to indicated row address 22, 75, 82 and column addresses adjacent to (or displaced by a predefined offset from) indicated column address 22, 76, 82. Preferably, the stored, incremented 114 column address is associated with a subsequent or adjacent column location in memory circuit 2. Hence, after burst mode 72, 73, 100 is defined, only a single column address 22, 76, 82 is necessarily indicated by $\overline{CAS}$ signal 24, 81.

To indicate which type of access is invoked (i.e., read or write), a burst mode/write enable ($\overline{BM/WE}$) signal 84 may be applied to memory circuit 2. For example, to write 71, 73 data 85 into memory circuit 2, $\overline{BM/WE}$ signal 84 may be held low 58, 65 or toggled; and to read 70, 72 data (DQ) 85 from memory circuit 2, $\overline{BM/WE}$ signal 84 may be held high or similarly toggled.

FIGS. 3 to 6 show representative timing diagrams for relevant signals (i.e., $\overline{RAS}$ signal 80, $\overline{CAS}$ signal 81, row and column address signal 82, $\overline{BE/OE}$ signal 83, $\overline{BM/WE}$ signal 84 and DQ signal 85) for operating memory circuit 2 respectively in page mode read 70, page mode write 71, burst mode read 72, and burst mode write 73. In each of such timing diagrams, vertical time slices 90-98 are drawn for illustrative purposes.

Also, for each of such timing diagrams, $\overline{RAS}$ signal 80 is applied 70 such that it transitions low at time 90, and transitions high at time 98; $\overline{CAS}$ signal 81 is applied 171, 172, 173, 174 such that it transitions low at time 91, high at time 92, low at time 93, high at time 94, low at time 95, high at time 96, low at time 97, and high at time 98; row address signal 82 is provided prior to time 90; and column address signal 76 is provided prior to time 91, until time 92. Note that in temporal correspondence with $\overline{CAS}$ signal 81, OE or WE signal may be toggled respectively during reading or writing operations.

Figure 3:
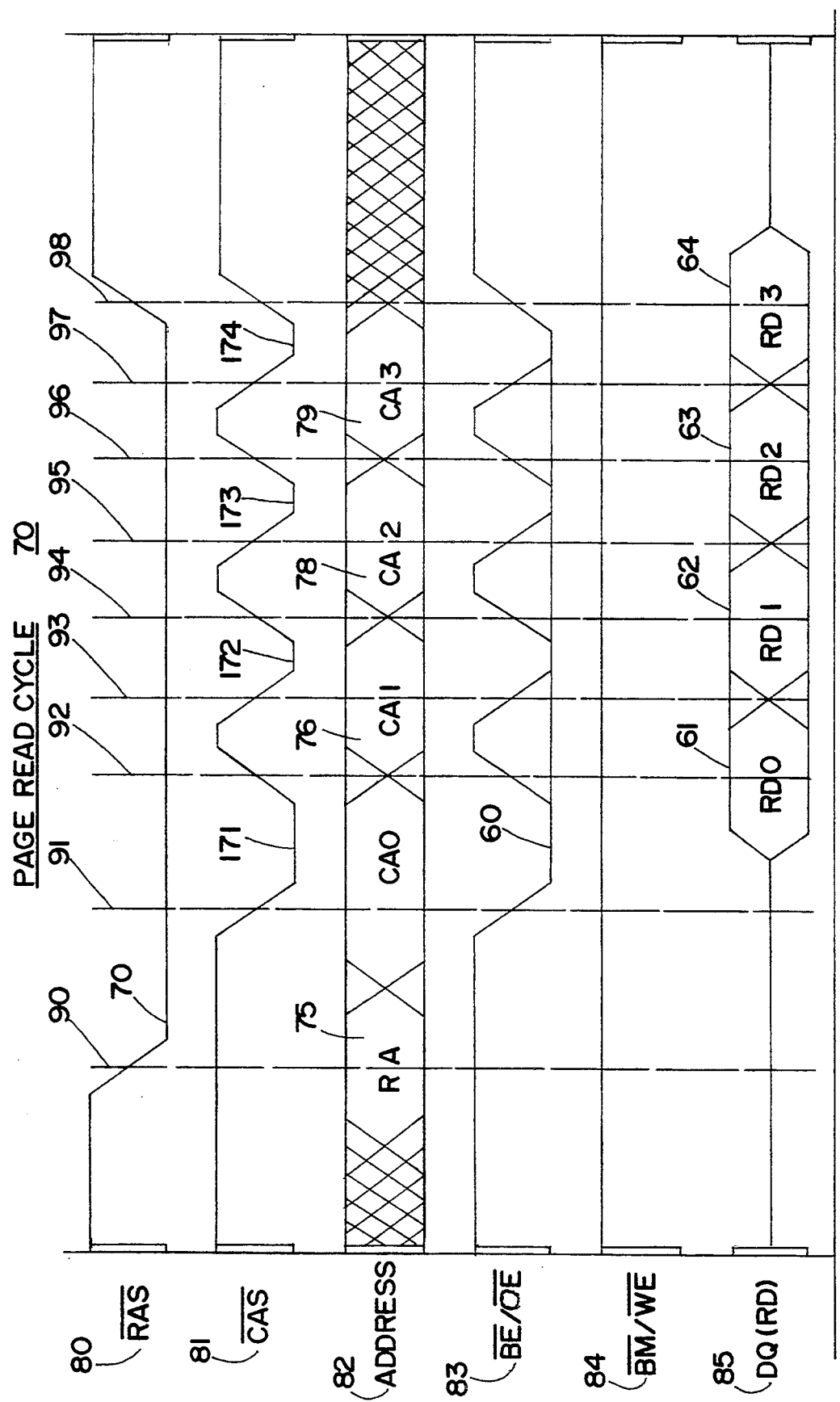
FIG. 3 is a timing diagram for relevant signals in operating memory circuit 2 in page mode read cycle 70, 120.
Figure 4:
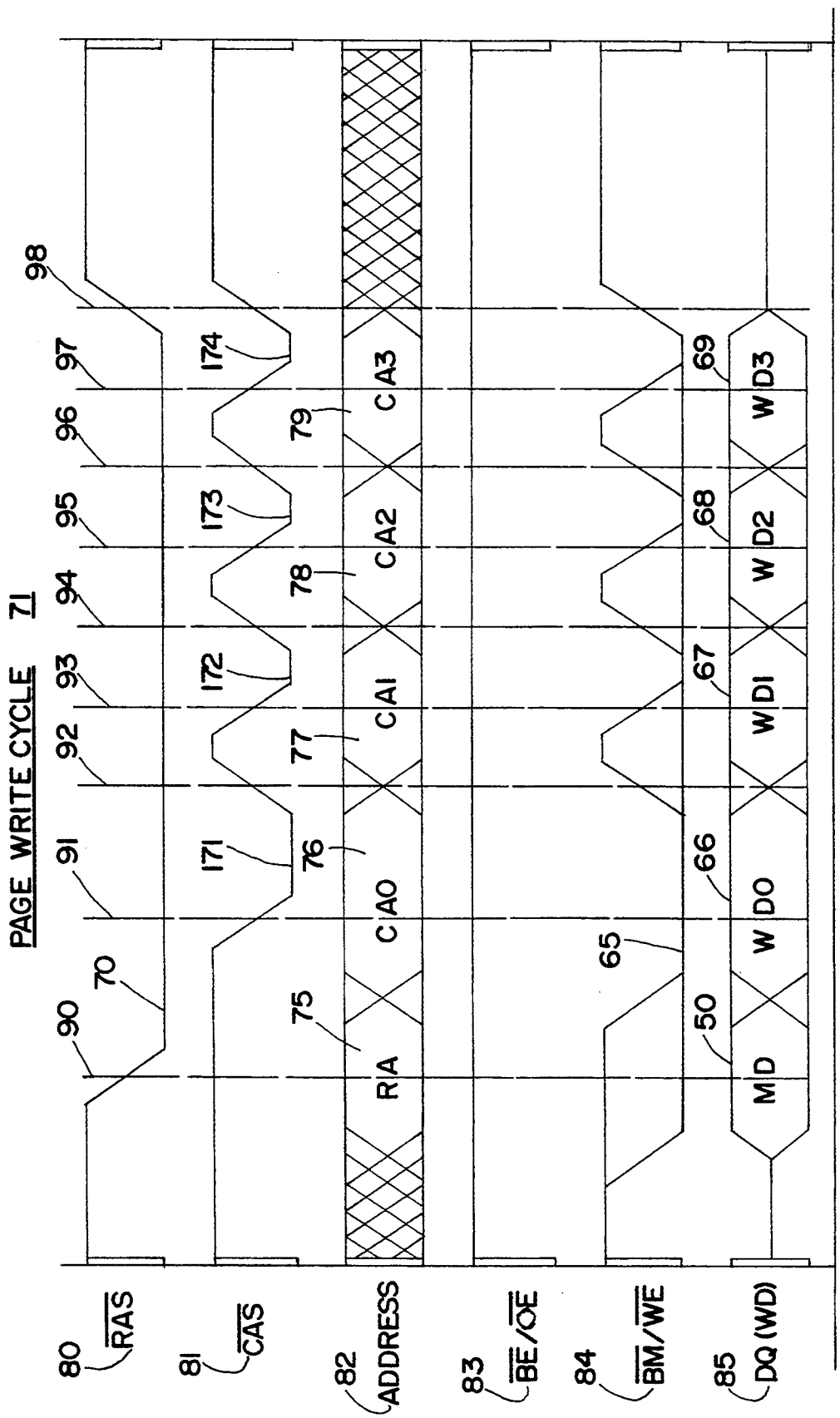
FIG. 4 is a timing diagram for relevant signals in operating memory circuit 2 in page mode write cycle 71, 120.

In the timing diagrams of FIGS. 3 and 4, page mode read 70 and page mode write 71 are illustrated. In particular, the definition of page mode 120 is indicated at time 90 during which $\overline{BE/OE}$ signal 83 remains high while $\overline{RAS}$ signal 80 is applied 70, as detected by burst mode detector 16 in memory circuit 2. Thus, while operating in page mode 120, memory circuit 2 may access storage locations associated with a single row address 75 and a number of column addresses 76, 77, 78, 79, applied while $\overline{RAS}$ signal 80 remains low 70 and $\overline{CAS}$ signal 81 is applied 171, 172, 173, 174 (or more times) correspondingly to column addresses 76-79.

To operate in page mode read 70, as shown in FIG. 3, $\overline{BM/WE}$ signal 84 is held high, and $\overline{BE/OE}$ signal 83 (which in page mode 120 (read or write), operates as a conventional DRAM output enable signal) is held low 60 from time 91 to time 98 or toggled, to enable output of DQ signal 85, thereby enabling memory circuit 2 to generate read-out data (RD0) 61, (RD1) 62, (RD2) 63, (RD3) 64, which correspond respectively with data stored in and readable from column addresses associated with CA0 76 to CA3 79.

In comparison, to operate in page mode write 71, as shown in FIG. 4, $\overline{BM/WE}$ signal 84 is held low 65 from time 90 to time 98 or toggled, and $\overline{BE/OE}$ signal 83 is held high, to enable input of DQ signal 85, thereby enabling memory circuit 2 to write in data (WD0) 66, (WD1) 67, (WD2) 68, (WD3) 69, which each correspond respectively with data to be written into column addresses associated with CA0 76 to CA3 79.

Figure 5:
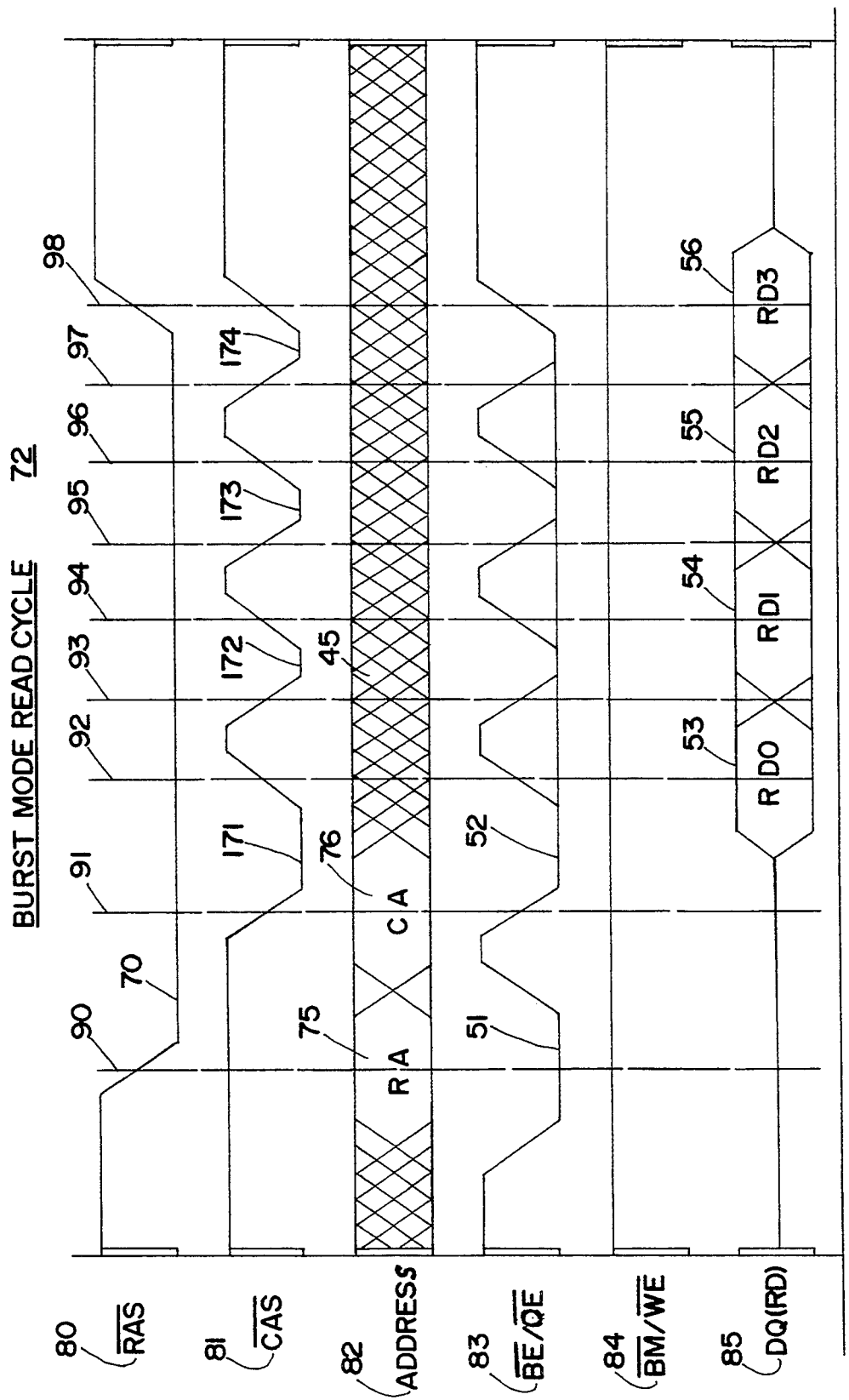
FIG. 5 is a timing diagram for relevant signals in operating memory circuit 2 in burst mode read cycle 72, 110.
Figure 6:
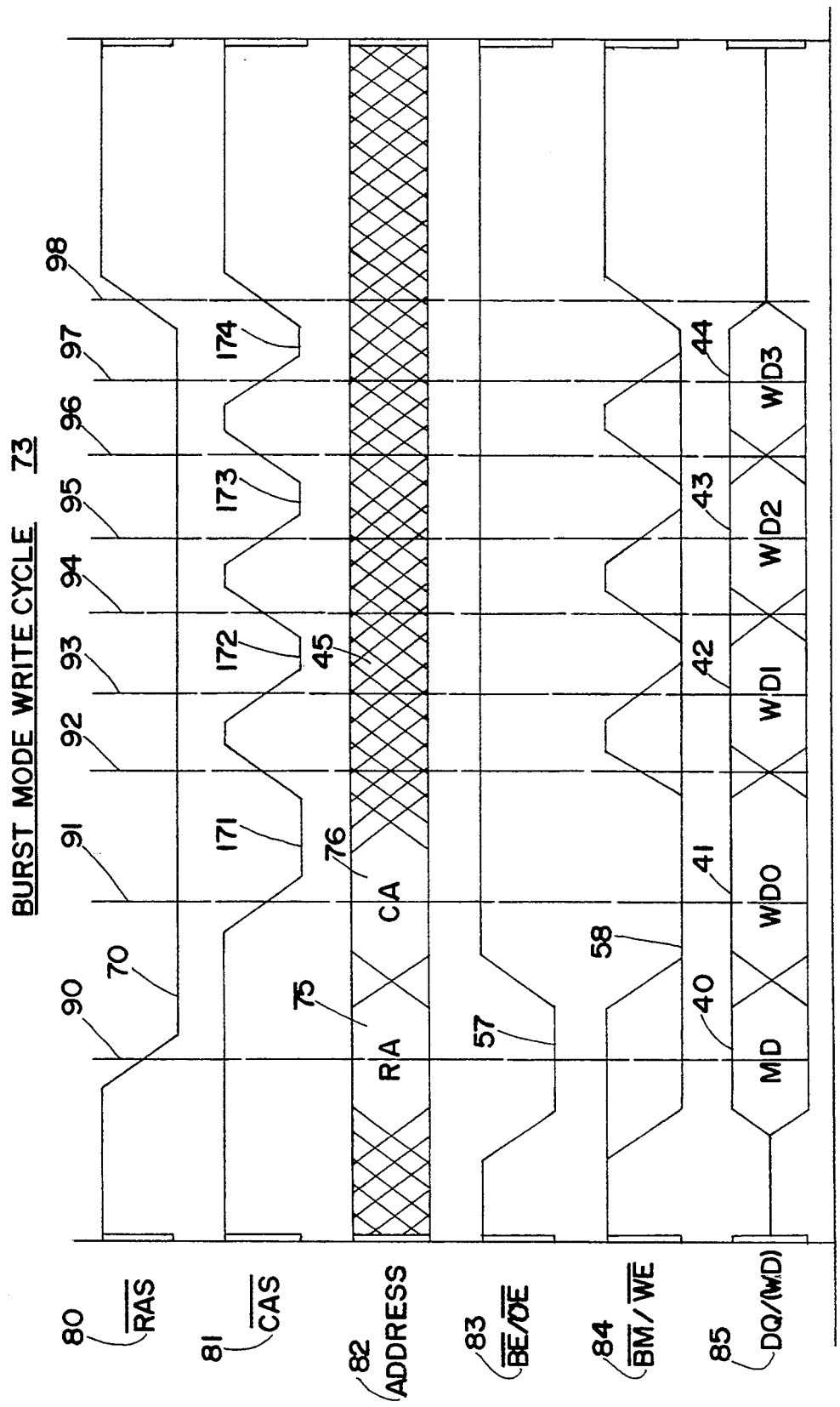
FIG. 6 is a timing diagram for relevant signals in operating memory circuit 2 in burst mode write cycle 73, 110.

In the timing diagrams of FIGS. 5 and 6, burst mode read 72 and burst mode write 73 are illustrated. In particular, the definition of burst mode 110 is indicated at time 90 during which $\overline{BE/OE}$ signal 83 is applied low 51, 57 while $\overline{RAS}$ signal 80 is applied 70, as detected by burst mode detector 16 in memory circuit 2. Thus, while operating in burst mode 110, memory circuit 2 may access storage locations associated with a single row address 75 and a number of column addresses, which preferably are sequentially adjacent to column address 76. While $\overline{RAS}$ signal 80 remains low 70 and $\overline{CAS}$ signal 81 is applied 171 initially, preferably during its falling edge at time 91, column address signal 76 is stored in address counter 14.

Unlike during page mode 120 operation, subsequent address signals 82 are disregarded 45 by memory circuit 2, i.e., as "don't care" signals, during burst mode 110 operation. In addition, subsequent $\overline{CAS}$ signal 81 applications 172, 173, 174 (or more times), likewise during its changing (i.e., rising and/or falling) edges at times 91, 92, 93, 94, 95, 96, 97, are each detected by burst mode detector 16, which then sets internal timing for address counter 14 to increment, during each detected $\overline{CAS}$ signal 81 rising or falling edge, the stored column address value to an adjacent column address for subsequent accessing.

To operate in burst mode read 72, as shown in FIG. 5, $\overline{BM/WE}$ signal 84 is held high, and $\overline{BE/OE}$ signal 83 is held low 52 from time 91 to time 98 or toggled, as well as 51 during time 90 when $\overline{RAS}$ signal 80 is applied. In burst mode 110 (read or write), $\overline{BE/OE}$ signal 83 does not operate as a conventional DRAM output enable signal, but rather as a burst mode 110 indicator prior to time 91, i.e., until $\overline{CAS}$ signal 81 is applied initially. In this way, $\overline{BE/OE}$ signal 83 enables output of DQ signal 85 and thus allows memory circuit 2 to generate read-out data (RD0) 53, (RD1) 54, (RD2) 55, (RD3) 56, which each correspond respectively with data stored in column addresses associated with CA0 76 and subsequently incremented corresponding column addresses (i.e., CA0+1, CA0+2, etc.).

In comparison, to operate in burst mode write 73, as shown in FIG. 6, $\overline{BM/WE}$ signal 84 is held low 58 from time 90 to time 98 or toggled; and $\overline{BE/OE}$ signal 83 is held high, to enable input of DQ signal 85, except during time 90 when $\overline{BE/OE}$ signal 83 is applied low 57 while $\overline{RAS}$ signal 80 is applied 70. In this way, memory circuit 2 may write out data (WD0) 41, (WD1) 42, (WD2) 43, (WD3) 44, which correspond respectively with data to be written from column addresses associated with CA0 76 and subsequently incremented corresponding column addresses (i.e., CA0+1, CA0+2, etc.).

We claim:

1. A method for operating a storage device, the method comprising the steps of:

applying a burst enable signal to the storage device;
applying a first address signal to the storage device during a selected time, said first address signal indicating a row address in the storage device, said first address signal being applied by a row address strobe ($\overline{RAS}$) signal applied to the storage device, wherein a burst mode is defined when the $\overline{RAS}$ signal is applied while the burst enable signal is applied;

detecting the definition of the burst mode by sampling a state of the burst enable signal when the $\overline{RAS}$ signal is applied;

applying a second address signal to the storage device, said second address signal indicating a column address in the storage device, said second address signal being applied by a column address strobe ($\overline{CAS}$) signal applied to the storage device; and accessing the storage device according to the first and second address signals.

2. A method for operating a storage device, the method comprising the steps of:

applying a burst enable signal to the storage device;
applying a first address signal to the storage device during a selected time, said first address signal indicating a row address in the storage device, said first address signal being applied by a row address strobe ($\overline{RAS}$) signal applied to the storage device, wherein a burst mode is defined when the $\overline{RAS}$ signal is applied while the burst enable signal is applied and a page mode is defined when the $\overline{RAS}$ signal is applied while the burst enable signal is disabled;

applying a second address signal to the storage device, said second address signal indicating a column address in the storage device, said second address signal being applied by a column address strobe ($\overline{CAS}$) signal applied to the storage device; and accessing the storage device according to the first and second address signals.

3. The method of claim 2 wherein:

the burst enable signal is applied as an output enable signal.

4. A method for accessing a storage device, said storage device comprising an asynchronously-accessible dynamic random access memory (DRAM) circuit having a matrix of digital storage locations arranged in rows and columns, the method comprising the steps of:

receiving a first address along a set of address lines;
receiving a second address along the address lines;
generating at least one burst address based on the second address;
applying the burst address to the storage device along a second set of address lines instead of the address lines; and
accessing a storage location within the storage device indicated by the first address and the burst address.

5. A storage device comprising:

a memory;
first address lines for receiving a row address and a column address;
a controller coupled to the address lines for generating at least one burst address based on the column address;
second address lines coupled to the controller for receiving the burst address; and
means coupled to the address and second address lines for accessing the memory according to the row address and the burst address.

6. The storage device of claim 5, wherein the column address and the burst address are sequential.

7. In a memory circuit, a burst mode controller comprising:

a signal detector for concurrently detecting a burst enable signal and a row address strobe signal ($\overline{RAS}$) to define a burst mode; and means for incrementing an accessed column address when a column address strobe $\overline{\text{CAS}}$ signal is applied during the burst mode.

8. The storage device of claim 7, wherein the controller receives a column address strobe $\overline{\text{CAS}}$ signal, and wherein the controller generates a plurality of burst addresses by incrementing the column address in response to toggling of the $\overline{\text{CAS}}$ signal.

9. A storage device, comprising:

a memory;

means for receiving a burst enable signal;

means for receiving a first address signal, said first address signal indicating a row address in the memory array, said first address signal being accompanied by a row address strobe ($\overline{\text{RAS}}$) signal, wherein a burst mode is defined when the $\overline{\text{RAS}}$ signal is received while the burst enable signal is received;

means for detecting the definition of the burst mode by sampling a state of the burst enable signal when the $\overline{\text{RAS}}$ signal is received;

means for receiving a second address signal, said second address signal indicating a column address in the memory array, said second address signal being accompanied by a column address strobe ($\overline{\text{CAS}}$) signal; and means for accessing the memory array according to the first and second address signals.

10. A storage device comprising:

a memory;

first address lines for receiving a row address and a column address;

a controller coupled to the address lines for generating at least one burst address based on the column address, the controller comprising:

a signal detector for concurrently detecting a burst enable signal and a row address strobe signal ($\overline{\text{RAS}}$) to define a burst mode; and means for generating a burst address when a column address strobe $\overline{\text{CAS}}$ signal is applied during the burst mode;

second address lines coupled to the controller for receiving the burst address; and means coupled to the first address and second address lines for accessing the memory according to the row address and the burst address.

* * * * *